US008658405B2

(12) United States Patent
Johal et al.

(10) Patent No.: US 8,658,405 B2
(45) Date of Patent: Feb. 25, 2014

(54) PROCESS FOR HYDROLYSIS OF WET FIBER AND METHOD FOR PRODUCING FERMENTATION PRODUCTS FROM WET FIBER

(75) Inventors: Sarjit Johal, Iowa City, IA (US); Steven L. Ramsden, Muscatine, IA (US); Zachary J. Halloran, Muscatine, IA (US); Albert J. Pollmeier, Muscatine, IA (US)

(73) Assignee: Grain Processing Corporation, Muscatine, IA (US)

( * ) Notice: Subject to any disclaimer, the term of this patent is extended or adjusted under 35 U.S.C. 154(b) by 125 days.

(21) Appl. No.: 13/028,908

(22) Filed: Feb. 16, 2011

(65) Prior Publication Data

US 2011/0201061 A1 Aug. 18, 2011

Related U.S. Application Data

(60) Provisional application No. 61/305,101, filed on Feb. 16, 2010.

(51) Int. Cl.
*D21B 1/16* (2006.01)

(52) U.S. Cl.
USPC ................... 435/161; 162/25; 162/26

(58) Field of Classification Search
USPC ................... 435/161, 15, 41; 162/26
See application file for complete search history.

(56) References Cited

U.S. PATENT DOCUMENTS

| | | | |
|---|---|---|---|
| 4,174,976 A | 11/1979 | Tsao et al. | |
| 4,242,455 A * | 12/1980 | Muller et al. | 435/162 |
| 4,281,063 A | 7/1981 | Tsao et al. | |
| 4,425,433 A * | 1/1984 | Neves | 435/163 |
| 4,708,746 A | 11/1987 | Hinger | |
| 5,338,366 A | 8/1994 | Grace | |
| 5,370,999 A * | 12/1994 | Stuart | 435/99 |
| 5,846,787 A | 12/1998 | Ladisch et al. | |

(Continued)

FOREIGN PATENT DOCUMENTS

| | | |
|---|---|---|
| WO | 2005079190 | 9/2005 |
| WO | 2006017786 | 2/2006 |

OTHER PUBLICATIONS

Beall, D.S., and Ingram, L.O., "Conversion of Hydrolysates of corn cobs and hulls into ethanol by recombinant *Escherichia coli* B containing integrated genes for ethanol production." Biotechnology letters, vol. 14 No. 9 (Sep. 1992), pp. 857-862.*

(Continued)

*Primary Examiner* — Jon P Weber
*Assistant Examiner* — Kara Johnson
(74) *Attorney, Agent, or Firm* — Fitch, Even, Tabin & Flannery LLP (57) ABSTRACT

Disclosed are a method of hydrolysis of wet fiber and a method for preparing ethanol. Generally, an agricultural plant material, such as corn hulls, distiller's dried grains, or spent germ, is treated to at least partially hydrolyze the fiber. The process may include a maceration step followed by a shearing operation in the presence of steam to yield a treated product, in which, in many embodiments, saccharides will be released and unbound from fibrous portions of the agricultural product. In some embodiments, the process includes macerating the material to provide a slurry having a solids content of at least 10 percent and jet cooking the slurry. A mixture of saccharides prepared in this fashion may be fermented to yield ethanol and/or biochemicals.

22 Claims, 3 Drawing Sheets

(56) References Cited

U.S. PATENT DOCUMENTS

| | | | |
|---|---|---|---|
| 7,494,675 | B2 | 2/2009 | Abbas et al. |
| 8,211,189 | B2* | 7/2012 | Guay et al. ............... 44/307 |
| 2003/0199049 | A1 | 10/2003 | Nguyen |
| 2003/0232109 | A1 | 12/2003 | Dawley et al. |
| 2005/0118692 | A1 | 6/2005 | Kinley et al. |
| 2006/0029702 | A1* | 2/2006 | McPherson et al. ......... 426/481 |
| 2008/0299256 | A1* | 12/2008 | Batie et al. ............... 426/52 |
| 2009/0143573 | A1 | 6/2009 | Olsen |
| 2010/0055741 | A1* | 3/2010 | Galvez et al. ............. 435/74 |

OTHER PUBLICATIONS

Beall et al., Conversion of hydrolysates of corn cobs and hulls into ethanol by recombinant *Escherichia coli* B containing integrated genes for ethanol production. Biotechnology Letters, vol. 14 No. 9 (Sep. 1992) pp. 857-862.*

Hendricks et al., Pretreatments to enhance the digestibility of lignocellulosic biomass. Bioresource Technology, vol. 100 No. 1 (Jan. 2009) pp. 10-18.*

Standard Sieve Series Specifications Woven Wire Cloth. Datasheet [online]. Screen Technology Group, Inc., 2009 [retrieved on Jul. 24, 2013]. Retrieved from the Internet:<URL:http://www.wovenwire.com/reference/screen-sieve-pr.htm>.*

Sulfuric Acid 93%. Datasheet [online]. Northstar Chemical, 2013 [retrieved on Jul. 25, 21013]. Retrieved from the Internet<http://www.northstarchemical.com/prod_sulfuricacid_prof.htm>.).*

Beall D S et al: "Conversion of hydrolysates of corn cobs hulls into ethanol by recombinant *Escherichia coli* B containing integrated genes for ethanol production", Biotechnology Letters, vol. 14, No. 9, 1992, pp. 857-862.

Lawford H G et al: "Fuel ethanol from corn residue prehydrolysate by a patented ethanologenic *Escherichia coli* B." Biotechnology Letters, vol. 14, No. 5, May 1992, pp. 421-426.

PCT International Search Report and Written Opinion—PCT/US2011/025070, dated Aug. 19, 2011.

Moiser et al—Industrial scale-up of pH-controlled liquid hot water pretreatment of corn fiber for fuel ethanol production; Laboratory of Renewable Resources Engineering, Department of Agricultural and Biological Engineering, Purdue University—2004.

* cited by examiner

PROCESS FOR HYDROLYSIS OF WET FIBER AND METHOD FOR PRODUCING FERMENTATION PRODUCTS FROM WET FIBER

CROSS REFERENCE TO RELATED APPLICATION

This application claims the benefit of U.S. Provisional Application No. 61/305,101, filed Feb. 16, 2010, which is incorporated by reference in its entirety.

TECHNICAL FIELD

The invention is in the field of processing agricultural and other plant-based materials.

BACKGROUND

Cereal crop biomass and fiber from agricultural processing operations include materials such as hulls, distillers' dried grains, and spent germ, as well as other postharvest debris. Historically, these materials typically have been used for ruminant fodder. The substantial value as well as quantity of biomass resources lost as ruminant fodder has become more apparent with the arrival of biofuels, particularly ethanol. Additionally, the biomass resources have been recognized to have potential value as a source of food ingredients, including nutritional and fiber products.

The technologies needed to convert biomass to biofuel have been the subject of study for at least three decades. Conventionally, the conversion of biomass fiber to ethanol is a multistep process. This process typically begins with the identification and collection of a suitable fiber material. A common feature of conventional process schemes is the hydrolysis of the biomass to produce a heterogeneous broth of fermentable carbohydrates and an array of biomolecules. This broth is subsequently fermented using a select microorganism to produce ethanol. The fermented broth then is distilled to recover the ethanol. The extracted broth typically is then concentrated, dried, and used in various applications, such as animal feed.

The biofuel industry has largely focused on simple readily available grain biopolymers, such as cereal starches. While starches will continue to be used, the realization that only a finite quantity of these can be diverted to the production of biofuels has resulted in a need for the identification and development of other feedstocks, particularly feedstocks that can be processed in economically viable methods.

Efforts have been made to develop new feedstocks and methods, but, in many instances, technologies developed in the laboratory are either cost prohibitive, challenging to scale up, or not robust enough to accommodate industrial practices and needs. In many instances, conventional processes can yield by-products that are detrimental to downstream processing steps.

SUMMARY

In some embodiments, methods are provided herein for hydrolyzing wet fiber. The starting fiber material may be minimally processed wet fiber from an agricultural processing operation, or other biomass, in lieu of or in addition to dried, ground and sized fiber solids. As described herein, wet fiber products, such as corn hulls and other agricultural materials, may be treated to hydrolyze the fiber. In a first stage, the fiber is macerated under acidic conditions, and in a second stage, the macerated fiber is subjected to a shearing force in the presence of steam, such as in a jet cooker. Advantageously, in one aspect, the maceration stage can yield a slurry that has a solids content of about 10 percent or more, yet has a viscosity that is suitable for jet cooking in the second stage. If desired, the maceration stage may include a shredding or grinding process under acidic conditions.

The macerated and sheared fiber product may itself be a commercially valuable product. In some cases, the process yields an enriched syrup or broth containing oligosaccharides, such as to arabinoxylans of varying sizes/lengths and monomers of xylan, arabinose, galactose and glucose. Also, in some embodiments, the process will yield an insoluble fiber that may be used as a dietary fiber in food, in pet food applications, or as a raw material for the production of prebiotics.

The enriched syrup or broth can be used as is in fermentation and feed applications or fractionated further. For instance, a mixture of oligosaccharides prepared in accordance with the above teachings can be inoculated with an ethanol-producing microorganism and fermented under appropriate conditions to generate ethanol. If desired, an ethanol fraction can then be recovered, such as by distillation. In one aspect, the invention provides a method for producing ethanol, comprising inoculating a saccharide mixture with a microorganism capable of fermenting the saccharides to produce ethanol; and fermenting the saccharide mixture, the saccharide mixture having been prepared via hydrolysis of wet fiber as described herein: In other embodiments, other fermentation products may be prepared via similar techniques but employing other microorganisms or substrates.

DETAILED DESCRIPTION

The methods provided herein utilize wet fiber material in a process to hydrolyze the fiber material and, in one particular aspect, to break down and solubilize the hemicellulose fraction of the fiber. As starting materials, fiber from cereal wet milling plants, such as from a corn wet milling operation, and dry grind fermentation plants, may be employed, and mixtures thereof. For example, corn hulls derived from a wet milling process can be used. Other suitable starting materials include, for example, germ, spent germ, distiller's dry grains, and other post harvest debris.

It is believed that the fiber material may have any water content, but, in many embodiments, the fiber material is "wet," that is, as supplied from a wet milling process without a forced drying step. In one aspect, the wet fiber is free flowing fiber. In one aspect, the water content of the wet fiber may be at least 20 percent; in other embodiments, at least 25 percent; in other embodiments, at least 30 percent; in other embodiments, at least 35 percent; in other embodiments, at least 40 percent; in other embodiments, at least 45 percent; in other embodiments, at least 50 percent; in other embodiments, at least 55 percent; in other embodiments, at least 60 percent; and in other embodiments, at least 65 percent. In some embodiments, the fiber may include a range of water contents, such as a range of about 20 to about 70 percent; in another aspect, about 40 to about 60 percent.

Figure 1:
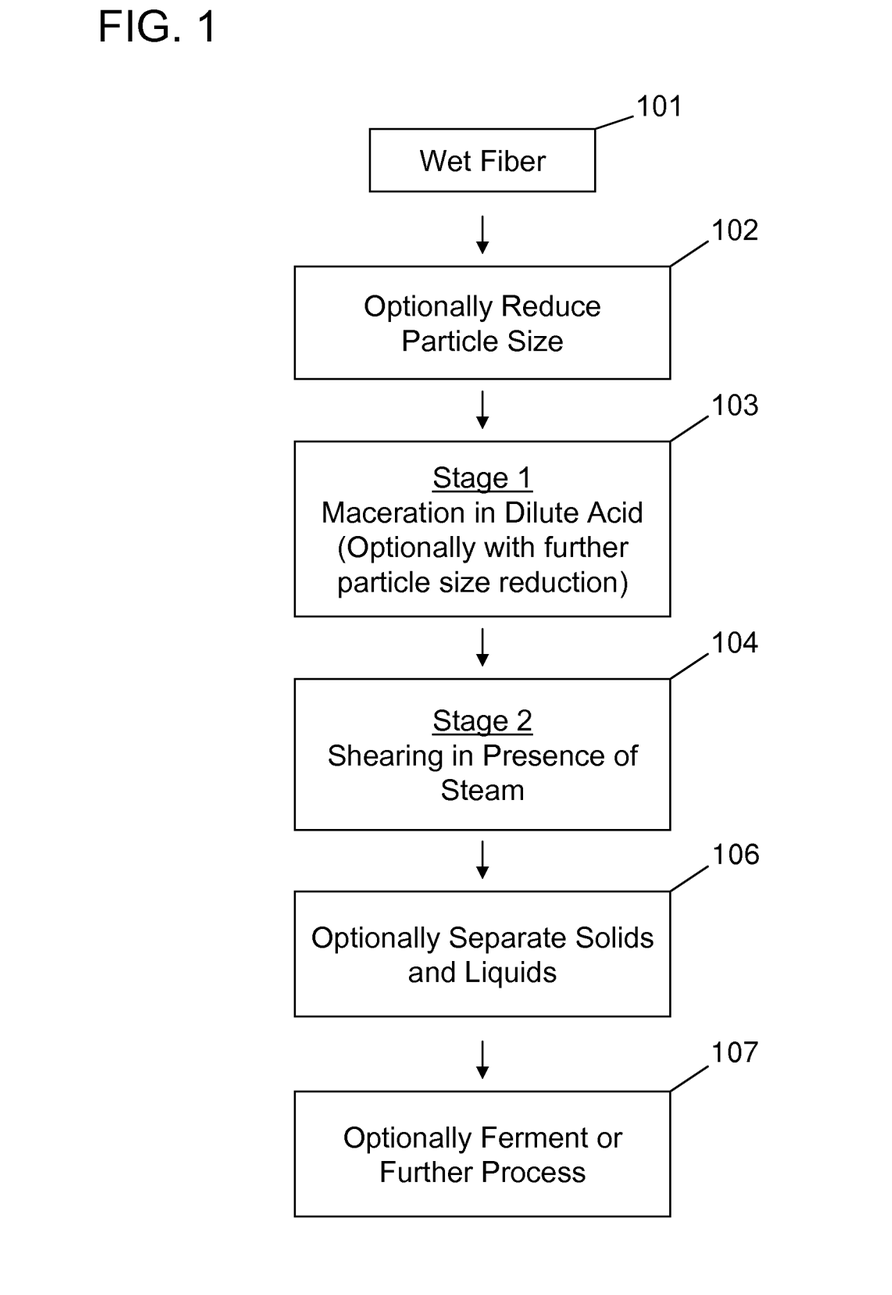
FIG. 1 is a flowchart that illustrates generally steps in a method for a wet fiber hydrolysis as described herein.

In the exemplary method shown in the flowchart of FIG. 1, wet fiber is treated in a two stage hydrolysis process. If desired, additional steps may be performed before, during or after the hydrolysis stages, and in some embodiments it is contemplated that steps may be omitted or combined. By one approach and as shown in FIG. 1, wet fiber 101 is preferably treated in step 102 to reduce the particle size of the fiber prior to the first hydrolysis stage 103, where the wet fiber is macerated in dilute acid to provide a fibrous slurry. First hydrolysis stage 103 preferably includes further particle size reduction, such as by grinding or shearing of the wet fiber material. After first hydrolysis stage 103, the fibrous slurry is treated in second hydrolysis stage 104 by shearing in the presence of steam. The sheared wet fiber can then be further processed, if desired, such as by step 106 to separate the solids and liquids and by step 107 to ferment or otherwise further process the separated solids or liquids.

Figure 2:
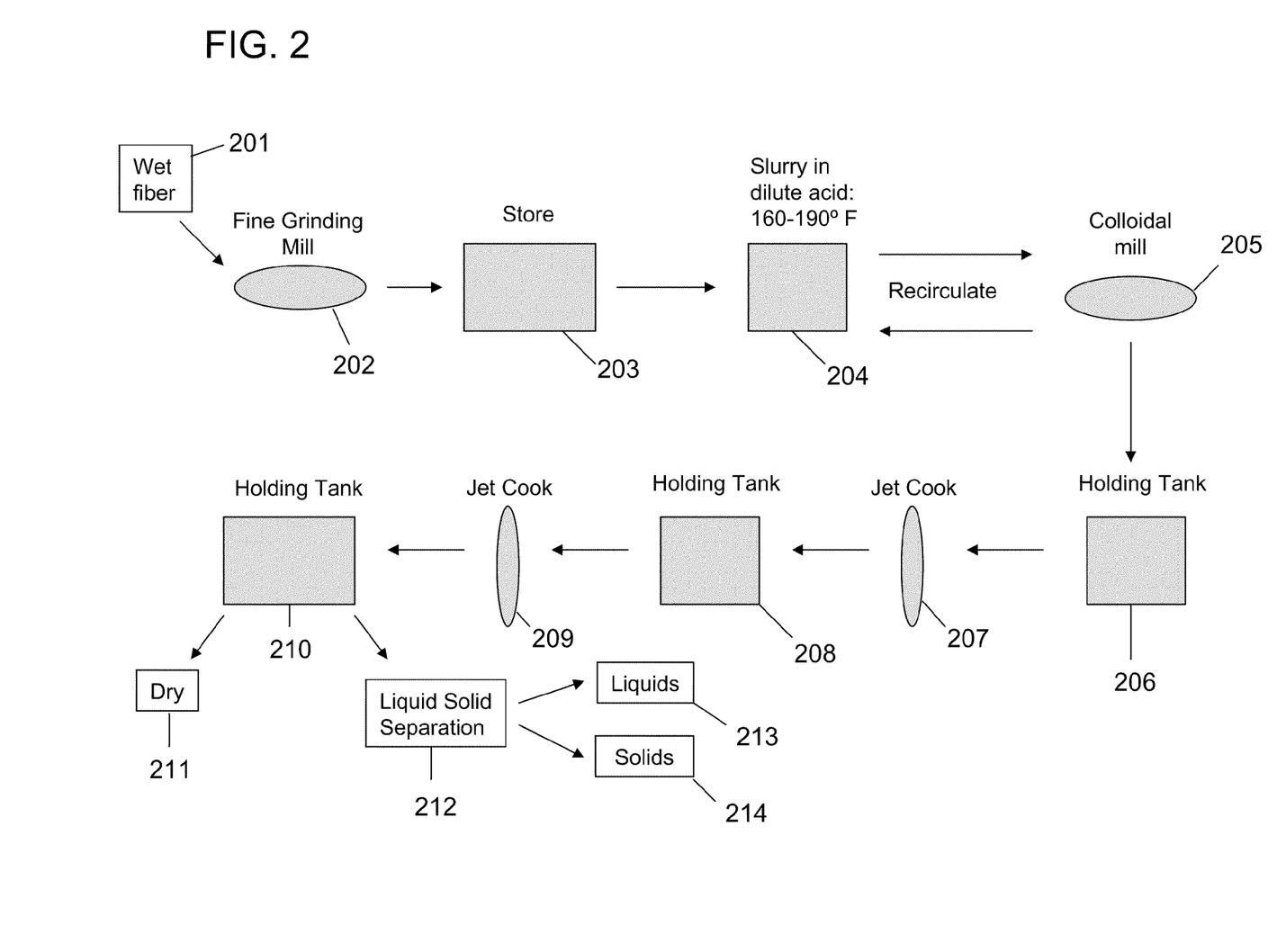
FIG. 2 is a schematic illustration of a system useful for accomplishing wet fiber hydrolysis as described herein.

In the system illustrated in FIG. 2, wet fiber 201 is treated by fine grinding mill 202 to reduce the particle size of the wet fiber. If desired, the wet fiber 201 can then be stored in storage container 203 prior to step 204 where the wet fiber is slurried in dilute acid at about 70 to about 90° C. The slurried fiber can then be treated with colloidal mill 205. The slurried fiber can be recirculated through the colloidal mill, if desired, to further reduce the particle size of the fiber. The slurried fiber may be placed in holding tank 206 prior to step 207, where the slurried fiber is jet cooked. If desired, the slurried fiber may be placed in holding tank 208 prior to further jet cooking step 209 and can be held in holding tank 210 after jet cooking. The jet cooked wet fiber can be dried in drying step 211 or treated by step 212 to separate liquids 213 from solids 214.

The fiber is hydrolyzed to yield a mixture of saccharides, which, for purposes of the present invention, include mono-, di-, and higher saccharides, by dissociation of these saccharides from plant cells in the fiber. Without intending to limit the invention to a particular theory of operation, it is believed that methods described herein include the use of thermal and chemical treatment in combination with two or more dissociative processes, one dissociative process occurring in the first stage and one dissociative process occurring in the second stage. In one or both of the dissociative processes, the fiber is contacted with steam while travelling at a high velocity. Augmenting thermochemical methods with multiple shearing and/or shredding forces with the addition of steam is believed to increase the decomposition of the fiber matrix.

Thermochemical hydrolysis of the fiber is believed to influence the quality and quantity of carbohydrate liberated and ultimately available for fermentation. The thermochemical conditions used to degrade the hemicellulose fraction should balance dissociation and the irreversible modification of released monosaccharides and other small molecules. For example, extremely harsh conditions can produce byproducts such as furfural, hydromethylfurfural, and organic acids such as acetic acid, ferulic acid, and coumaric acid. In some cases, these and other degradation products can interfere with enzymatic reactions or downstream processes such as fermentation, particularly fermentation for production of ethanol. In addition, the overall quality of the composition may be compromised for select applications such as feed, or as raw material for fractionation of value of components.

The consequences of using harsh treatments manifest themselves in terms of direct inhibitory (e.g., biological) outcomes but also as potential costs associated with removal and/or sequestering of these materials. While complete removal is virtually impossible at the industrial scale, it is difficult to establish clear standards for scale-up and operation. For instance, even if the known and/or major inhibitors can be substantially removed, it is highly probable that inhibitors will persist given the complexity of the heterogeneous broth produced from breaking down the fiber. Prior to the methods provided herein, the absence of precisely controlled thermochemical processes and systems and clear scale-up objectives complicate and substantially increase the costs and risks. Alternatively, overly mild conditions may be insufficient to produce monomers from intermediate polymeric structures such as oligosaccharides as well as open the fiber matrix sufficiently to allow access for cellulosic and associated enzymes. Hence, there appears to be an equilibrium that needs to be attained in order to maximize the yield and the quality of the carbohydrate syrup obtained from hydrolysis. Fiber breakdown conditions can be varied by adjusting one or all of the following variables: starting material preparation, incubation, and high shear steam treatment. Specific variables within each stage can also be modified to select the degree of breakdown or liquefaction of the fiber. For example, during the stage of maceration, process variables, including incubation time, fiber addition rate, temperature, chemical (e.g., acid or alkali) and concentration, shearing/milling system forces such as maceration, shredding, or high shear specific methods, can all be modified to provide the desired degree of fiber breakdown. Exemplary parameters are described hereinbelow; for other processes and systems, those skilled in the art should follow the guidelines and teachings set forth herein.

Depending on the particle size of the starting wet fiber material, it may be desirable to screen and size the fiber prior to maceration. In one aspect, a particle separation system, such as a vibratory separator or comparable system, can be used. In another aspect, the starting wet fiber material can be milled or otherwise treated to attain a median particle size in the range of about 100 to about 1000 microns, more preferably in the range of about 200 to about 800 microns and even more preferably about 250 to about 500 microns. For example, as supplied, corn hulls from a wet milling operation may have an average particle size of about 1.2 to about 1.3 mm, as evaluated via successive screening measurements. The corn hulls can be milled to provide an average particle size of about half the original particle size. A pin mill is preferably employed. In one aspect, the wet fiber is not dried prior to decreasing the median particle size of the wet fiber material, which advantageously permits costs associated with drying the fiber or with obtaining a more processed or purified product to be avoided. In another aspect, no additional water is added to the wet fiber prior to particle size reduction.

In one embodiment, the first stage, or maceration stage, of hydrolysis can be accomplished by treatment of the wet fiber with dilute acid under conditions of shear. For example, shear can be provided by a variety of techniques or devices, including but not limited to a high speed mixer, continuous inline shearing or multi-pass shearing. In one aspect, the acid may include sulfuric acid, hydrochloric acid, citric acid, phosphoric acid, or combinations thereof. In another aspect, the acid is a dilute mineral acid solution, such as but not limited to sulfuric acid, hydrochloric acid, or combination thereof. In many cases, the acid will be a food grade acid, such as citric, hydrochloric, phosphoric acid, or a combination thereof.

In one aspect, the wet fiber is added into a dilute acid solution to a final solids concentration of about 5 to about 25 percent dry solids basis, more preferably 8 to 22 percent dry solids basis, and even more preferably 10 to 18 percent dry solids basis. In one aspect, the dilute acid solution including the wet fiber contains about 0.5 to about 12 weight percent acid, about 2 to about 9 weight percent acid in another aspect, and about 3 to about 6 weight percent acid in yet another aspect, and has a pH of about 0.5 to about 2, preferably about 1.0 to about 1.9, and more preferably about 1.4 to about 1.9. In one aspect, the wet fiber is macerated in the dilute acid solution for about 20 minutes to about 3 hours and, in another aspect, for about 30 minutes to about 2 hours.

In yet another aspect, the dilute acid liquid mixture can be maintained at a temperature between about 30 to about 95° C., preferably about 45 to about 90° C., and more preferably about 65 to about 90° C. throughout maceration. By one approach, the fiber material can be added to a temperature controlled vessel, such as a steam-jacketed tank, containing the dilute acid at a temperature of 30 to 95° C., more preferably about 45 to about 90° C. to provide a fibrous slurry.

In one aspect, the starting material can be metered into the dilute acid solution over a defined interval to provide a rate of addition that maintains an approximately constant slurry viscosity throughout the material addition stage. By one approach, the slurry viscosity can be measured using a Newport Scientific Rapid Visco Analyser at about 65 to about 90° C. The method of addition is not particularly limited. For example, linear, stepwise, or batch addition, among other methods, can be used if desired. It is known that incubating fiber in a mineral acid solution causes a reduction in the water absorbency and water holding capacity. The loss of water holding capacity results in a lower solution/slurry viscosity and reflects the degradation of hemicelluloses. The resultant increase in solution fluidity and water availability contributes to better agitation/mixing with shorter retention times at higher solids.

In some embodiments, the maceration step provides for the release of some amount of the total bound hemicellulose in the fiber, such as about 25 to about 70 percent. In other embodiments, about 25 to about 35 percent of the total bound hemicellulose in the fiber is released.

By one approach, after maceration, the slurry has a viscosity of about 400 to about 680 cP as measured with a Newport Scientific Rapid Visco Analyser at 90° C. Generally, a slurry having a viscosity of about 300 to about 700 cP is typically suitable for jet cooking. Advantageously, the viscosity is achieved at higher solids content than is possible without macerating wet fiber in dilute acid.

In some aspects, the maceration step may yield a slurry that has a solids content of 10 percent or more, yet is of a suitable viscosity for jet cooking. In other aspects, the solids content may be at least about 11 percent, in some aspects at least about 12 percent, in some aspects at least about 13 percent, in some aspects at least about 14 percent, in some aspects at least about 15 percent, in some aspects at least about 16 percent, in some aspects at least about 17 percent, in some aspects at least about 18 percent, in some aspects at least about 19 percent, and in other aspects at least about 20 percent, all while having a viscosity suitable for jet cooking. Depending on the viscosity and solids content of the slurry, it may be desirable to add water to the slurry to reduce the solids content prior to the second stage of hydrolysis, but generally, even with added water, the solids content is at least about 10 percent or more.

Subsequently, it is preferable that the fibrous mixture is thoroughly mixed with grinding, shredding and/or shearing forces, such as by using a grinding, shearing or milling system, including but not limited to a colloidal mill, dispersing grinder, high volume shearing pump, or similar equipment capable of quickly and efficiently shearing and shredding the material at elevated temperatures, such as about 30 to about 95° C. By one approach, the slurry can be recirculated through the grinding or milling system for 2 to 6 passes, preferably 2-3 passes, using a pump, such as a Moyno or piston pump, capable of handling viscous solution. The use of grinding, shredding and/or shearing forces in the maceration stage reduces the particle size of the wet fiber prior to the second stage. Such treatment can yield a slurry that can be jet cooked at a higher solids content, such as at least 10 percent or more. By macerating the fibrous slurry under conditions of grinding or shear, a higher solids content can be attained while retaining pumpability. This ability to pump, and hence to jet cook, the slurry at such solids content, coupled with the ability to begin with wet material (i.e., without the necessity of a drying step) is believed, at least in some embodiments, to provide certain economic advantages. For instance, the described process can permit a reduction in process water and waste water requirements, permit a reduction in plant sizing and operating costs, and reduce costs for removing water from the end product.

The macerated, fibrous slurry is then treated in a second stage of hydrolysis with shearing in the presence of steam. For example, a jet cooking or comparable high speed shearing system/technology that permits the fiber to be sheared in the presence of steam can be used. By one approach, the macerated slurry is heated to a temperature and at a pressure effective to liberate hemicellulose, in some cases, a temperature between about 140 to about 160° C. under a pressure of about 35 to about 105 psig for a short period on the order of about 5 to about 60 minutes, in other embodiments about 5 to about 30 minutes, and in other embodiments about 5 to about 20 minutes, using a jet cooking system. Jet cooking provides efficient shearing and heating with direct steam and continuous flow through a combining tube. In jet cooking, high pressure saturated steam, ranging from about 60 to about 200 psig, can be injected through a steam nozzle into the center of a venturi mixing tube. The slurry mass is pulled into the annulus gap formed by the steam nozzle and venturi opening. The slurry is heated as it accelerates to sonic velocity within the mixing tube. During passage through the mixing tube, the fiber is subjected to extreme turbulence which strips off fiber constituents and ultimately causes fracturing, dissociation, release of soluble biomolecules and refinement/cleansing of insoluble components of the fiber mosaic.

While multiple passes, preferably 2-5 and more preferably 2-3 passes, are typically required to dissociate and release the soluble and insoluble content from the fiber, a single pass can be used if the desired amount of dissociation of the soluble components and stripping of the insoluble contents is achieved. In some aspects, a higher number of passes, such as 3-7 passes, may be necessary to fully affect complete dissociation of the soluble components and stripping of the insoluble elements. In one aspect, multiple passes can be used such as by recycling through a single cooker or through the use of several jet cookers arranged in-line. In some embodiments, the two stage hydrolysis process described herein is effective to hydrolyze the hemicellulose in the wet fiber. In one aspect, at least about 10 percent of the soluble solids are monomers, in another aspect at least about 15 percent of the soluble solids are monomers, in another aspect at least about 20 percent of the soluble solids are monomers, and in yet another aspect at least about 25 percent of the soluble solids are monomers. In other embodiments, the monomers account for at least about 8 percent, in another aspect at least about 10 percent, in another aspect at least about 12 percent, in another aspect at least about 14 percent, and in another aspect at least about 16 percent of the total solids.

While not intending to limit the invention to a particular theory of operation, it is believed that, at least in some aspects, the processing of the fiber in accordance with the methods described herein can improve the accessibility of denaturants by using disruptive forces. The array of tightly packed biomolecules of the fiber is held together by various chemical forces. Consequently, application of multiple mechanical forces concurrently or in rapid succession is believed to offer the greatest potential for disrupting and reducing the production of undesired byproducts. Also, use of a two stage process can allow for reduction of duration and amount of chemical used in the process, thereby reducing chemical exposure and less undesirable byproduct production.

In one aspect, the process provides a paste-like slurry or suspension containing soluble and insoluble components, the soluble components including saccharides. It is believed that these saccharides principally result from breakdown of hemicellulose in the fiber, these saccharides including hemicellulose byproducts such as arabinoxylans of varying sizes/lengths and monomers of xylan, arabinose, galactose and glucose. If desired, the resulting slurry or suspension may be separated into solid and liquid phases using known liquid-solid separation techniques. The resulting product is a mixture of a fibrous material and unbound nutritive material that has a number of commercial uses. If desired, the fibrous material may be separated from the unbound nutritive material. Both the fibrous material and the nutritive material may be useful as food ingredients. The liquid phase may be fermented or may be further treated, while the solid phase may be employed as a food fiber product or may be treated enzymatically to break down the cellulose. The carbohydrate fractions can then be pooled or fractionated after treatment, if desired.

In one aspect, the solids portion comprises mostly cellulose, with little unbound hemicellulose or starch, and in which the liquid portion contains hemicellulose, sugars, and soluble carbohydrates. It is believed that the cellulose portion will not be substantially degraded in many embodiments.

In another aspect, the described methods can provide an enriched syrup or broth containing oligosaccharides including, but not limited to, that are readily fermented by microorganisms to produce ethanol or other fermentation products. The enriched syrup or broth can be used in fermentation and feed applications, or may be fractionated further.

By one approach, the syrup or broth can be inoculated with an ethanol producing microorganism and fermented under appropriate conditions to generate ethanol. In one aspect, the microorganism selected produces ethanol as a major fermentation product. Any suitable yeast or bacteria culture can be used. The fermented broth can be further treated, such as by distilling, to recover an ethanol fraction. The remainder of the distilled broth can also be further treated, such as by drying or concentrating, and used in various applications, such as in animal feed.

By another approach, the syrup or broth can be inoculated with microorganisms under appropriate conditions to generate other desired products, such as acids and other biochemicals, from C5 and C6 sugars in the syrup or broth. For example, succinic acid, malic acid, 3-hydroxy propionic acid, glucaric acid, sorbitol, xylitol, aspartic acid, glutamic acid, itaconic acid, glycerol, oxalic acid, and combinations thereof, can be produced from fermentation of the syrup or broth provided in the methods described herein. If desired, the product of the fermentation can be isolated using a variety of isolation techniques.

Another effect of the methods provided herein is an improvement in the efficiency of optional subsequent dissociative treatments, including but not limited to enzyme treatments for the production of fuel, feed and food. In addition, the conversion of fiber components to end products via fermentation, cell culture, fractionation and synthetic chemical processes is enhanced.

The insoluble fiber obtained from the methods described herein can be used, for example, as dietary fiber in food, pet food applications and as a raw material for the production of prebiotics.

Advantageously, the methods described herein can avoid the need for costly, specialized, small scale equipment such as homogenizers, presses, extruders, autoclaves and the like, and slow batch techniques, such as high temperature alkaline or acid hydrolysis in high volume, low solids applications, for purposes of breaking down the fiber.

Further, in many embodiments, a consequence of increasing process solids in the maceration stage is a reduction in the facilities process water and waste water requirements including but not limited to plant sizing and operating costs. This is particularly important in the production of commodity products such as ethanol, where even small improvements are amplified.

The following non-limiting Examples are provided to illustrate certain aspects of the methods provided herein.

Example 1

Particle Size Profile of Ground Corn Wet Fiber

Approximately five hundred grams of wet corn fiber at about 60-65 percent moisture (35-40 percent dry solids) was passed through a pin mill. This rapid, single pass treatment reduced the average particle size of the wet corn fiber from 1.27 mm (before milling) to 0.61 mm (after treatment). This reduction in particle size was sufficient to permit further processing without the need for drying and extensive milling.

Example 2

Wet Corn Hulls: Viscosities after Acid/Temperature Pre-Treatment

Acid pretreatment of corn hulls (wet milled) at various solids and acid contents were conducted batchwise for 60-75 minutes to observe for flowability (viscosity). All slurries started at 10 percent solids in the presence of dilute sulfuric acid (1 percent or 2 percent acid (v/v)) at a pH estimated to be about 1.2 to about 1.6. More solids were added as the acid/temperature treatment proceeded. This method of solids addition resulted in slurries with 15 percent to 18 percent solids. The slurries provided acceptable pumpability with viscosities of approximately 1200 cP, as shown in Table 1. Viscosities were measured with a Newport Scientific Rapid Visco Analyser at 50° C. and 70° C.

TABLE 1

Viscosity Measurements at Various Temperatures

| # | % Hull Solids | % Acid v/v | Viscosity @ 50° C. | Viscosity @ 70° C. |
|---|---|---|---|---|
| 1 | 10% Hulls (ds) | 1% | 270 cP | 220 cP |
| 2 | 15% Hulls (ds) | 1% | 1500 cP | 1320 cP |
| 3 | 18% Hulls (ds) | 2% | 2150 cP | 1140 cP |

(ds = dry solids)

Example 3

Wet Corn Hulls: Jet Cooking in a Pilot Facility

Wet corn hulls (originally 42 percent ds) that had been ground to a median particle size of about 500 microns while wet were slurried as described in Example 2 and successfully fed to a pilot scale jet cooking apparatus. The hulls were jet cooked at temperatures from about 125° C. to about 150° C. This study demonstrated that slurried wet corn hulls up to 12.5 percent dry solids ("ds") were pumpable through a jet cooker. The slurry feed contained ~1 percent v/v sulfuric acid.

The percent solids, free hemicellulose (ds), xylose, arabinose, and glucose were measured at various steps of the process, as described below. The results of those measurements are presented in Table 2 below.

TABLE 2

| Samples | Solids (%) | % Free Hemicellulose (ds) | Xylose (μg/g ds) | Arabinose (μg/g ds) | Glucose (μg/g ds) |
|---|---|---|---|---|---|
| Step 1 | 12.2 | 5.17 | 547.76 | 2702.41 | 621.36 |
| Step 2 | 14.8 | 4.61 | 2119.86 | 12718.94 | 2626.18 |
| Step 3 | 12.5 | 7.91 | 5273.46 | 24759.98 | 3389.05 |
| Step 4 | 12.4 | 17.99 | 17436.32 | 59338.81 | 5933.32 |
| Step 5 | 12.0 | 23.32 | 20994.44 | 56515.99 | 6239.61 |

Step 1: Starting wet slurry
Step 2: Addition of wet hulls to bring up solids
Step 3: Recirculation feed with attachment of orifice and use of a Moyno pump
Step 4: The first pass after jet cooking
Step 5: The second pass after jet cooking This example demonstrates the benefits imparted by jet cooking for hemicellulose degradation, as evidenced in steps 4 and 5.

Example 4

Processing Wet Corn Fiber from Milling to Jet Cooking

Two thousand pounds of wet corn fiber (60 percent moisture) recovered from a corn wet milling plant is quickly milled using a pin mill (or similar piece of equipment) to reduce the median particle size by about 50 percent to about 400 to about 450 microns.

Sufficient fiber (5-7 percent) is added to a 0.7 percent (w/v) sulfuric (or phosphoric) acid solution which is heated to about 75° C. to a viscosity that allows for aggressive mixing. Mixing and maceration are achieved somewhat concurrently using an overhead mixer, such as a Lightning mixer, in combination with a recycle loop that incorporates a Moyno pump and an inline mixer or similar device capable of shredding the fiber.

The slurry is incubated in the aforementioned system and viscosity monitored. When a decline in viscosity is noted, additional fiber is added to the macerated mixture. It is preferable to maintain a constant viscosity in the system through the metered conveyance of fiber, although bulk stepwise additions are acceptable. Sufficient fiber is added to achieve a final fiber content of about 17-20 percent (ds), which should be attainable in about 45 to about 60 minutes. Alternatively, this stage of the process can be run in a continuous mode using the slurry viscosity as a guide to control the rate of release and addition of dilute acid solution and fiber to the reaction vessel.

The macerated slurry next undergoes high shear jet cooking at about 150-160° C. for about 1-30 minutes. If higher shear is required, multiple passes through the jet cooking system can be used, either by recycling through a single cooker or through the use of several jet cookers arranged in-line.

The processed slurry can serve as a raw material for use in fermentations, such as ethanol fermentations. It also may be processed further to separate the soluble and insoluble components, with each fraction being used in a different application.

Example 5

Viscosity After Wet Fiber Size Reduction

Approximately 440 pounds of wet corn hull fiber with a moisture content range of 40-60 percent (dry solid basis) was collected directly from a line in a corn wet milling plant. Typically, the fiber is used within about 48-72 hours of collection, although longer storage times are possible.

Figure 3:
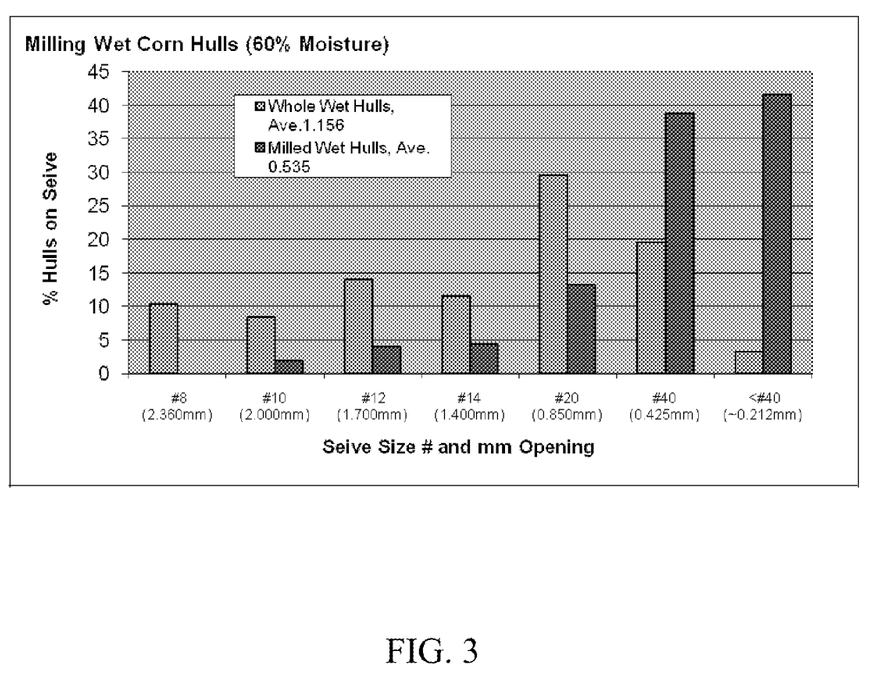
FIG. 3 is a chart with a particle size profile achieved with a Prater fine grind mill in accordance with Example 5.

A Prater fine grind mill was used to reduce particle size of the wet hulls. The wet hulls were manually fed into a pilot scale fine grind mill. The unit can also be equipped with a vacuum feed system for continuous operation. The Prater mill, and similar fine grinding mills, utilizes a high speed impact principle to achieve a narrow distribution of finished particle sizes. A typical particle size profile achieved is shown in FIG. 3.

The effect of reduction of fiber size on fiber solubility, thermochemical response and flow dynamics was examined by determining solution viscosity. Viscosity of milled and unmilled wet corn hulls is shown in Table 3. Viscosity was measured at 35° C., 55° C., 75° C., and 95° C. with a Newport Scientific Rapid Visco Analyser.

TABLE 3

| | Whole Wet Corn Hulls 5%, Dry Solids Basis | Milled - One Pass 10%, Dry Solids Basis |
|---|---|---|
| 35° C.* | 5050 cP | 132 cP |
| 55° C.* | 1750 cP | 100 cP |
| 75° C.* | 1135 cP | 90 cP |
| 95° C.* | 650 cP | 160 cP |

*Slurry temperature used for viscosity measurement

Milling of the wet fiber in the manner described alters the solution/fluid characteristics of the slurried fiber at all of the temperatures tested. As demonstrated by the viscosity data, size reduction facilitates processing by lowering viscosity which facilities pumping as well as allowing for higher solids content.

Example 6

Wet Fiber Maceration

This example illustrates the first stage of shearing and wet fiber maceration following the preliminary size reduction of the wet fiber.

Wet fiber prepared as described in Example 5 was added to a steam jacketed vessel holding about 800 pounds of water containing about 6 percent (wt/solids ds) sulfuric acid to yield a pH of about 1.6. The temperature of the dilute acid solution was adjusted to about 77° C. prior to fiber addition. The fiber was added to the solution with vigorous mixing.

After allowing about 15 minutes for temperature equilibration, the slurry was pumped through an in-line colloidal mill, such as a pilot plant scale Dicon colloidal mill. The contents of the vessel received two passes through the mill at a flow rate of about 500 liters/hour. Temperature and agitation in the holding vessel were kept constant throughout this process. The results of this treatment are shown in Table 4 and 5.

TABLE 4

Solids Content

| Sample | Temperature (° F.) | Solids (%) | % Soluble Solids | % Insoluble Solids |
|---|---|---|---|---|
| Start | 185 | 14.64 | 25.1 | 74.9 |
| First Pass | 175 | 14.84 | 40.2 | 59.8 |
| Second Pass | 180 | 15.52 | 45.5 | 54.5 |

TABLE 5

Carbohydrate Analysis of Hydrolysis

| Sample | Soluble Solids (% ds) | Carbohydrate | % of Total Solids | % of Soluble Solids |
|---|---|---|---|---|
| Start | 25.1 | Total | 58.75 | |
| | | Soluble | 16.87 | 67.21 |
| | | Monomer | 2.89 | 11.51 |
| First Pass | 40.2 | Total | 57.29 | |
| | | Soluble | 28.64 | 71.24 |
| | | Monomer | 3.74 | 9.30 |
| Second Pass | 45.5 | Total | 57.63 | |
| | | Soluble | 35.05 | 77.03 |
| | | Monomer | 5.78 | 12.70 |

The dispersing grinder (an in-line colloidal mill) subjected the sized fiber to intense shear and agitation. The shearing forces serve to enhance contact with the hot, dilute acid solution leading to a substantial breakdown of the fiber structure in a quick and efficient manner. The disruption of the fiber structure by macerating and dispersing the solids into the acid solution is shown by the increase in percent soluble solids and decline in percent insoluble solids, both with respect to total solids as well as specific fractions, such as carbohydrates.

Example 7

Jet Cooking

This example illustrates the second stage of wet fiber hydrolysis used after the colloidal mill treatment. The sheared product of Example 6 was passed through the Dicon colloidal mill a second time and then jet cooked with two passes at about 150° C. with a five minute residence time for each pass.

The solids content, including soluble and insoluble solids, was measured after a second pass with the Dicon mill, as well as after the first and second passes in the jet cooker. The results are presented in Table 6 below. The carbohydrate content was measured by HPLC and the results are presented in Table 7.

TABLE 6

Solids Content

| Sample | Temperature (° C.) | Solids (%) | Soluble Solids (%) | Insoluble Solids (%) |
|---|---|---|---|---|
| Dicon Mill - Second Pass | 82 | 15.52 | 45.5 | 54.5 |
| Jet Cook - First pass | 150 | 14.81 | 67.2 | 32.8 |
| Jet Cook - Second Pass | 150 | 14.71 | 66.5 | 33.5 |

TABLE 7

Carbohydrate Analysis

| Sample | Soluble Solids (% ds) | Carbohydrate | % of Total Solids | % of Soluble Solids |
|---|---|---|---|---|
| Dicon Mill - Second Pass | 45.5 | Total | 57.63 | |
| | | Soluble | 35.05 | 77.03 |
| | | Monomer | 5.78 | 12.70 |
| Jet Cook - First Pass* | 67.2 | Total | 56.98 | |
| | | Soluble | 55.23 | 82.19 |
| | | Monomer | 21.27 | 31.65 |
| Jet Cook - Second Pass* | 66.5 | Total | 57.77 | |
| | | Soluble | 56.52 | 84.99 |
| | | Monomer | 34.13 | 51.32 |

*Used 5 minute residence time for jet cooking.

Tables 6 and 7 show that each stage of hydrolysis leads to sequential degradation of the corn hull fiber. For example, wet fiber is dissociated to a median particle size of about 400 to 500 microns and used generate a slurry predominantly composed of insolubles. The slurry is then treated in a relatively mild manner to yield a slurry with increased levels of solubles, which range from higher order soluble structures to monomers. This ordered degradation reduces the need for harsh single stage treatments which can lead to production of very heterogeneous compositions and the generation of inhibitory compounds that can interfere with enzymatic reactions or downstream processes, such as fermentation, in ethanol production. In addition, this is advantageously accomplished using commercially available, installed systems that are widely used in many agricultural processing operations.

Example 8

Summary of Results from Pilot Plant Scale Trials Using a 4 Percent Dilute Sulfuric Acid Solution Fiber was obtained from a corn wet milling plant and generally processed as described in Example 5. The fiber was slurried and macerated as described in Example 6, except 4 percent sulfuric acid is used instead of 6 percent sulfuric acid. After maceration, the fiber was hydrolyzed by jet cooking as described in Example 7. The solids and carbohydrate contents were measured as described in Example 7. The results are presented in Tables 8 and 9.

TABLE 8

Solids Content

| Sample | Temperature (° C.) | Solids (%) | % Soluble Solids | % Insoluble Solids |
|---|---|---|---|---|
| Start | 77 | 13.94 | 17.1 | 82.9 |
| First Pass | 80 | 13.86 | 21.2 | 78.8 |
| Second Pass | 85 | 14.23 | 24.5 | 75.5 |
| Jet Cook - First Pass | 150 | 14.20 | 42.9 | 57.1 |
| Jet Cook - Second Pass | 150 | 13.93 | 52.7 | 47.3 |
| Jet Cook - Third Pass | 150 | 13.00 | 61.1 | 38.9 |

TABLE 9

Carbohydrate Analysis

| Sample | Soluble Solids (% ds) | Carbohydrate | % of Total Solids | % of Soluble Solids |
|---|---|---|---|---|
| Start | 4.5 | Total | 54.62 | |
| | | Soluble | 11.15 | 65.20 |
| | | Monomer | 0.71 | 4.15 |
| First Pass | 21.2 | Total | 54.87 | |
| | | Soluble | 13.49 | 63.63 |
| | | Monomer | 1.20 | 5.66 |
| Second Pass | 24.5 | Total | 49.72 | |
| | | Soluble | 16.70 | 68.16 |
| | | Monomer | 3.56 | 14.53 |
| Jet Cook - First Pass* | 42.9 | Total | 53.68 | |
| | | Soluble | 32.12 | 74.87 |
| | | Monomer | 9.51 | 22.17 |
| Jet Cook - Second Pass* | 52.7 | Total | 55.08 | |
| | | Soluble | 41.58 | 78.90 |
| | | Monomer | 15.26 | 28.96 |
| Jet Cook - Third Pass* | 61.1 | Total | 54.51 | |
| | | Soluble | 45.82 | 74.99 |
| | | Monomer | 16.77 | 27.45 |

*Used jet cooking residence times of 10 minutes for the first pass and 5 minutes for the second and third passes.

The results of this integrated wet fiber hydrolysis trial are consistent with the pattern of hydrolysis described in Examples 6 and 7, albeit at a lower acid concentration.

Example 9

Ethanol Production

Yeast is added to the slurry of saccharides prepared from the third pass pilot scale run of Example 8, and this slurry is fermented to yield ethanol. An ethanol fraction is recovered upon distillation.

It is thus seen that a method for hydrolysis of wet fiber is provided.

Uses of singular terms such as "a," "an," are intended to cover both the singular and the plural, unless otherwise indicated herein or clearly contradicted by context. The terms "comprising," "having," "including," and "containing" are to be construed as open-ended terms. All references, including publications, patent applications, and patents, cited herein are hereby incorporated by reference. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A method comprising:
   providing a wet fiber material having a water content of about 20 to about 70 percent;
   macerating the wet fiber material under acidic conditions in a first processing unit to provide a slurry having a solids content of at least about 10 percent after maceration and a viscosity suitable for pumping, the solids content being greater than preparing the wet fiber under acidic conditions without macerating;
   pumping the slurry to a second processing unit; and
   shearing the slurry in the presence of steam in the second processing unit.

2. The method of claim 1, further comprising decreasing the average particle size of the wet fiber material to 100 to about 1000 microns prior to macerating the wet fiber material.

3. The method of claim 1, wherein the wet fiber material is macerated in an acid solution having a pH of about 0.5 to about 2.0.

4. The method of claim 3, wherein the wet fiber material is macerated in an acid solution having a pH of about 1.0 to about 1.9.

5. The method of claim 1, wherein macerating further comprises decreasing the average particle size of the slurry prior to shearing the slurry in the presence of steam.

6. The method of claim 1, wherein macerating is carried out at about 30° C. to about 95° C.

7. The method of claim 6, wherein macerating is carried out at about 45° C. to about 90° C.

8. The method of claim 1, wherein the wet fiber material has a water content of about 40 to about 60 percent.

9. The method of claim 1, wherein the wet fiber material is an agricultural plant material selected from the group consisting of wet corn hulls, distiller's dried grains, spent germ, and combinations thereof.

10. The method of claim 9, wherein the wet fiber material is wet corn hull fiber.

11. The method of claim 1, wherein macerating is carried out by use of at least one device selected from the group consisting of colloidal mill, dispersing grinder, and high volume shearing pump.

12. The method of claim 1, said shearing comprising jet cooking the slurry.

13. The method of claim 12, wherein slurry is jet cooked to a temperature between about 140° C. to about 160° C. under a pressure of about 35 to about 105 psig.

14. The method of claim 1, wherein macerating is conducted until about 25 to about 35 percent of total bound hemicellulose of the wet fiber material is released.

15. The method of claim 1, wherein the acid is selected from the group consisting of sulfuric, hydrochloric, citric, phosphoric, and combinations thereof.

16. A method comprising:
   providing a wet fiber material having a water content of about 20 to about 70 percent;
   macerating the wet fiber material under acidic conditions and under grinding, shredding and/or shearing in a first processing unit to provide a slurry having a solids content of at least about 10 percent after maceration and a viscosity suitable for pumping;

pumping the slurry to a second processing unit; and shearing the slurry in the presence of steam in the second processing unit.

17. The method of claim 16, wherein the wet fiber material is an agricultural plant material selected from the group consisting of wet corn hulls, distiller's dried grains, spent germ, and combinations thereof.

18. The method of claim 17, wherein the wet fiber material is wet corn hull fiber.

19. A method comprising:

providing a wet fiber material having a moisture content of at least about 20 wt %;

decreasing the average particle size of the wet fiber material to 100 to about 1000 microns;

macerating the wet fiber material under acidic conditions and under grinding, shredding and/or shearing in a first processing unit to provide a slurry, the slurry having a solids content of at least about 10% and a viscosity suitable for pumping; and pumping the slurry to a second processing unit; and shearing the slurry in the presence of steam in the second processing unit.

20. The method of claim 19 wherein the slurry has a viscosity in the range of about 400 to about 680 cp.

21. The method of claim 19, wherein the wet fiber material is an agricultural plant material selected from the group consisting of wet corn hulls, distiller's dried grains, spent germ, and combinations thereof.

22. The method of claim 21, wherein the wet fiber material is wet corn hull fiber.

\* \* \* \* \*